(12) United States Patent
Hepworth

(10) Patent No.: US 11,937,942 B2
(45) Date of Patent: Mar. 26, 2024

(54) WEARABLE ARTICLE AND METHOD OF MAKING THE SAME

(71) Applicant: Prevayl Innovations Limited, Manchester (GB)

(72) Inventor: Isabel Rose Hepworth, Paris (FR)

(73) Assignee: Prevayl Innovations Limited, Manchester (GB)

( * ) Notice: Subject to any disclaimer, the term of this patent is extended or adjusted under 35 U.S.C. 154(b) by 0 days.

(21) Appl. No.: 17/916,905

(22) PCT Filed: Apr. 19, 2021

(86) PCT No.: PCT/GB2021/050926
§ 371 (c)(1),
(2) Date: Oct. 4, 2022

(87) PCT Pub. No.: WO2021/214434
PCT Pub. Date: Oct. 28, 2021

(65) Prior Publication Data
US 2023/0128957 A1    Apr. 27, 2023

(30) Foreign Application Priority Data

Apr. 20, 2020 (GB) .................... 2005694
Apr. 20, 2020 (GB) .................... 2005699
May 28, 2020 (GB) .................... 2008007

(51) Int. Cl.
*A61B 5/00* (2006.01)
*A41C 3/00* (2006.01)
(Continued)

(52) U.S. Cl.
CPC .......... *A61B 5/6804* (2013.01); *A41C 3/0057* (2013.01); *A41D 1/002* (2013.01);
(Continued)

(58) Field of Classification Search
CPC ......... A61B 5/6804; A61B 5/27; A61B 5/002; A61B 2562/227; A41C 3/0057;
(Continued)

(56) References Cited

U.S. PATENT DOCUMENTS 9,242,093 B1    1/2016  Sherman
2004/0060092 A1    4/2004  Bennett
(Continued)

FOREIGN PATENT DOCUMENTS

CN    108175394    6/2018
CN    208850692    5/2019
(Continued)

OTHER PUBLICATIONS

International Search Report received in PCT/GB2021/050926 dated Jul. 9, 2021.
(Continued)

*Primary Examiner* — Adam Z Minchella
(74) *Attorney, Agent, or Firm* — Suzannah K. Sundby, Esq.; Canady + Lortz LLP

(57) ABSTRACT

The wearable article 100 comprises an inner fabric layer 101 and an outer fabric layer 111 overlapping the inner fabric layer 101 to form an overlapping region 121. An electronics component 200*a*, 200*b* is disposed at least partially between the inner and outer fabric layer 101, 111 in the overlapping region 121. The inner fabric layer 101 comprises an opening 143*a*, 143*b* to expose part of the electronics component 200*a*, 200*b*.

20 Claims, 10 Drawing Sheets

(51) Int. Cl.
*A41D 1/00* (2018.01)
*A41D 13/12* (2006.01)
*A41D 27/20* (2006.01)
*A61B 5/24* (2021.01)
*A61B 5/27* (2021.01)

(52) U.S. Cl.
CPC ....... *A41D 13/1281* (2013.01); *A41D 27/205* (2013.01); *A61B 5/002* (2013.01); *A61B 5/27* (2021.01); *A41D 2500/10* (2013.01); *A41D 2500/20* (2013.01); *A61B 2562/227* (2013.01)

(58) Field of Classification Search
CPC .. A41D 1/002; A41D 13/1281; A41D 27/205; A41D 2500/10; A41D 2500/20
See application file for complete search history.

(56) References Cited

U.S. PATENT DOCUMENTS

| | | | |
|---|---|---|---|
| 2006/0135863 A1* | 6/2006 | Birnbaum | A61B 5/6804 600/388 |
| 2009/0227856 A1 | 9/2009 | Russell | |
| 2012/0238910 A1* | 9/2012 | Nordstrom | A61B 5/0002 600/587 |
| 2013/0131484 A1* | 5/2013 | Pernu | A61B 5/28 600/388 |
| 2015/0119675 A1* | 4/2015 | Kaneko | A61B 5/6804 600/388 |
| 2016/0135516 A1 | 5/2016 | Cobbett | |
| 2016/0143424 A1 | 5/2016 | Stephens | |
| 2017/0238634 A1 | 8/2017 | Berns | |
| 2018/0049698 A1 | 2/2018 | Berg | |
| 2018/0160751 A1 | 6/2018 | Epp Frenette | |
| 2018/0255636 A1 | 9/2018 | Seo | |
| 2018/0271441 A1* | 9/2018 | Dabby | A61B 5/6804 |
| 2020/0046047 A1 | 2/2020 | Bentley | |
| 2023/0145601 A1 | 5/2023 | Hepworth | |

FOREIGN PATENT DOCUMENTS

| | | |
|---|---|---|
| CN | 110840581 | 2/2020 |
| CN | 210782989 | 6/2020 |
| DE | 202019003510 | 10/2019 |
| EP | 2505090 | 10/2012 |
| EP | 3510922 | 7/2019 |
| GB | 2594256 | 10/2021 |
| WO | 2004110192 | 12/2004 |
| WO | 2009013704 | 1/2009 |
| WO | 2010083462 | 7/2010 |
| WO | 2014165997 | 10/2014 |
| WO | 2016054386 | 4/2016 |
| WO | 2018115726 | 6/2018 |
| WO | 2019022646 | 1/2019 |

OTHER PUBLICATIONS

Written Opinion received in PCT/GB2021/050926 dated Jul. 9, 2021.
Prosecution history of GB2594335.
Search and Examination Report received in GB2005699 dated Sep. 29, 2020.
Search Report received in GB GB2005695.8 dated Nov. 3, 2020.
Search Report received in GB2008005.7 dated Nov. 24, 2020.
U.S. Appl. No. 17/918,219 and prosecution thereof.
U.S. Appl. No. 17/924,848 and prosecution thereof.
International Search Report received in PCT/GB2021/050927 dated Jul. 21, 2021.
Written Opinion received in PCT/GB2021/050927 dated Jul. 21, 2021.
International Search Report received in PCT/GB2021/051267 dated Aug. 18, 2021.
Written Opinion received in PCT/GB2021/051267 dated Aug. 18, 2021.

* cited by examiner

WEARABLE ARTICLE AND METHOD OF MAKING THE SAME

The present invention is directed towards a wearable article and method of making the same and a wearable article that incorporates an electronics component such as an electrode.

CROSS-REFERENCE TO RELATED APPLICATIONS

This application claims priority from United Kingdom Patent Application number 2005694.1 filed on 20 Apr. 2020, United Kingdom Patent Application number 2005699.0 filed on 20 Apr. 2020 and United Kingdom Patent Application number 2008007.3 filed on 28 May 2020, the whole contents of which are incorporated herein by reference.

BACKGROUND

Wearable articles can be designed to interface with a wearer of the article, and to determine information such as the wearer's heart rate, rate of respiration, activity level, and body positioning. Such properties can be measured with a sensor assembly that includes a sensor for signal transduction and/or microprocessors for analysis. The articles include electrically conductive pathways to allow for signal transmission between an electronics module for processing and communication and sensing components of the article. The wearable articles may be garments. Such garments are commonly referred to as 'smart clothing' and may also be referred to as 'biosensing garments' if they measure biosignals.

US 2018/0049698A1 discloses a garment manufactured by bonding an adhesive to a first layer of fabric and a second layer of fabric. Holes are cut into each layer of fabric to accommodate the integration of sensors and a mount for a processing unit. Conductive thread embroidered onto a support layer is bonded to the adhesives of the second layer of the fabric. The support layer is removed such that the conductive thread remains bonded to the adhesive. The conductive thread is exposed within each hole, and the mount and sensors can be coupled within the holes such that an electrical connection is established between the mount and at least one sensor via the conductive thread.

It is desirable to overcome at least some of the problems associated with the prior art, whether explicitly discussed herein or otherwise.

SUMMARY

According to the present disclosure there is provided a wearable article and method as set forth in the appended claims. Other features of the invention will be apparent from the dependent claims, and the description which follows.

According to a first aspect of the disclosure, there is provided a wearable article. The wearable article comprises an inner fabric layer. The wearable article comprises an outer fabric layer overlapping the inner fabric layer to form an overlapping region. The wearable article comprises an electronics component disposed at least partially between the inner and outer fabric layer in the overlapping region. The inner fabric layer comprises an opening to expose part of the electronics component.

Advantageously, the electronics component is sandwiched (partially or fully) between the inner and outer fabric layers of the wearable article. Separate insulating layers are not required as the inner fabric layer performs the insulating function and protects against aspects of the electronics component from contacting a skin surface when worn. The inner fabric layer comprises at least one opening to expose part of the electronics component. This enables part of the electronics component such as a sensing region of the electronics component to contact the skin surface when worn.

The electronics component may only be exposed at one or more opening in the inner fabric layer. The remainder of the electronics component may be sandwiched between the inner and outer fabric layers.

The electronics component may comprise a conductive pathway. The conductive pathway may comprise conductive wires, transfers, traces, or conductive yarn.

The inner fabric layer may cover the conductive pathway. The inner fabric layer may insulate the conductive pathway and prevent the conductive pathway from coming into direct contact with a skin surface when worn. The outer fabric layer may cover the conductive pathway.

The electronics component may comprise a sensing component. The opening may expose at least part of the sensing component. This enables the sensing component to measure a signal and optionally contact the skin surface when worn. The electronics component may comprise a plurality of sensing components. The inner fabric layer may comprise a plurality of openings. Each of the sensing components may be exposed by one of the openings of the inner fabric layer.

The sensing component may comprise an electrode. The opening may expose at least part of the electrode.

The opening may have a corresponding size to the sensing component. The sensing component may be aligned with the opening.

The sensing component may have an outer surface facing the outer fabric layer and an inner surface facing the inner fabric layer. The sensing component may comprise an electrode. The electrode may be provided on the inner surface.

The sensing component may comprise a connection terminal for connecting with an electronics module. The connection terminal is provided on the outer surface. The electronics module may be removably coupled to the wearable article.

The inner and outer fabric layers may be substantially the same size.

A pocket space may be formed between the inner and outer fabric layer in the overlapping region. The electronics component may be arranged such that when an electronics module is positioned in the pocket space, the electronics module is brought into communication with the electronics component.

The wearable article may further comprise a middle fabric layer disposed between the inner and outer fabric layers in the overlapping region. The pocket space may be formed between the inner and middle fabric layers in the overlapping region. The middle fabric layer may be the same size as the overlapping region.

The outer layer of the pocket space may form an attachment mechanism for holding the electronics module in communication with the electronics component.

The outer layer of the pocket space may comprise a stretch material and may form a pressure membrane arranged to apply pressure to the electronics module when located within the pocket space. The pressure may urge the electronics module into communication with the electronics component. The stretch material may comprise an elastomeric material.

The outer fabric layer may be unattached to the inner fabric layer in the vicinity of the pocket space to form an opening for the pocket space. The pocket space may be accessible from an outside surface of the wearable article. The pocket space may be accessible from a margin of the outer fabric layer.

The wearable article may further comprise a stretch material provided between the outer and inner fabric layers and arranged to tension the wearable article when worn. The stretch material may comprise an elastomeric material.

The wearable article may comprise a band arranged to surround a circumference of a wearer. The band may comprise the outer fabric layer and the inner fabric layer.

The wearable article may be a bra. The bra may comprise a front portion, a back portion and the band comprising the outer and inner fabric layers. The band may form an underband portion extending from a lower margin of the front portion and the back portion of the bra.

The band may form a chest strap arranged to surround a torso of the wearer.

The inner fabric layer may have first and second opposed margins. The outer fabric layer may have first and second opposed margins. The outer fabric layer may overlap part of the inner fabric layer in the overlapping region. The overlapping region may be bounded by the second margin of the inner fabric layer and the first margin of the outer fabric layer.

The inner fabric layer may be an upper portion and the outer fabric layer may be a lower portion.

The first margins of the upper and lower portions may be upper margins. The second margins of the upper and lower portions may be lower margins.

The overlapping region may extend between side margins of the upper and lower portions.

The wearable article may be a top.

According to a second aspect of the disclosure, there is provided an assembly comprising an electronics module and a wearable article of the first aspect of the disclosure.

According to a third aspect of the disclosure, there is provided a method of manufacturing a wearable article. The method comprises providing an inner fabric layer. The method comprises providing an outer fabric layer overlapping the inner fabric layer to form an overlapping region. The method comprises disposing an electronics component between the inner and outer fabric layer in the overlapping region. The inner fabric layer may comprise an opening to expose part of the electronics component.

BRIEF DESCRIPTION OF THE DRAWINGS

Examples of the present disclosure will now be described with reference to the accompanying drawings, in which.

DETAILED DESCRIPTION

Figure 1:
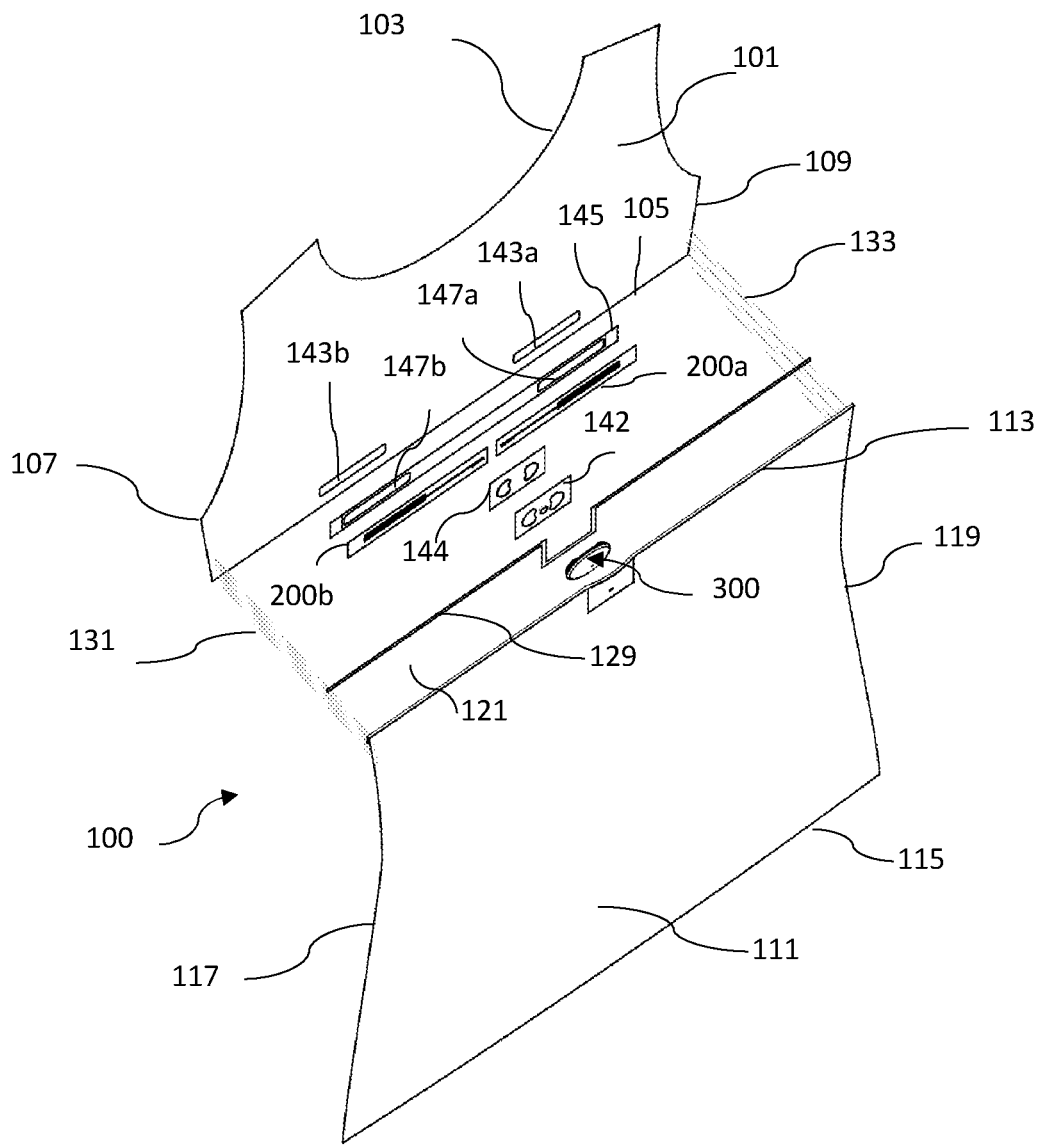
FIG. 1 shows an exploded front surface view of an example wearable article according to aspects of the present disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise.

"Wearable article" as referred to throughout the present disclosure may refer to any form of article which may be worn by a user. The wearable article may be a garment. The garment may refer to an item of clothing or apparel. The garment may be a top. The top may be a shirt, t-shirt, blouse, sweater, jacket/coat, or vest. The garment may be a dress, brassiere, shorts, pants, arm or leg sleeve, vest, jacket/coat, glove, armband, underwear, chest band, headband, hat/cap, collar, wristband, stocking, sock, or shoe, athletic clothing, personal protective equipment, swimwear, wetsuit or drysuit.

The garment may be a tight-fitting garment. Beneficially, a tight-fitting garment helps ensure that the sensor devices of the garment are held in contact with or in the proximity of a skin surface of the wearer. The garment may be a compression garment. The garment may be an athletic garment such as an elastomeric athletic garment.

The wearable articles may be constructed from natural fibres, synthetic fibres, or a natural fibre blended with one or more other materials which can be natural or synthetic. The yarn may be cotton. The cotton may be blended with polyester and/or viscose and/or polyamide according to the application. Silk may also be used as the natural fibre. Cellulose, wool, hemp, and jute are also natural fibres that may be used in the wearable article. Polyester, polycotton, nylon and viscose are synthetic fibres that may be used in the wearable article.

Referring to FIGS. 1 to 5, there is shown a front section 102 (FIG. 2) of a wearable article 100 according to aspects of the present disclosure. The wearable article 100 is arranged to cover a torso of a wearer when worn. The wearable article 100 in this example is a sleeveless shirt also known as a tank top, singlet, or vest.

The front section 102 of the wearable article 100 covers the front of the wearer when worn. A back section 104 (FIG. 2) of the wearable article 100 may also be provided to cover the back of the wearer. The front section 102 may be not connected to the back section 104 directly, or a pair of side sections may be provided connecting the front section 102 to the back section 104.

Figure 2:
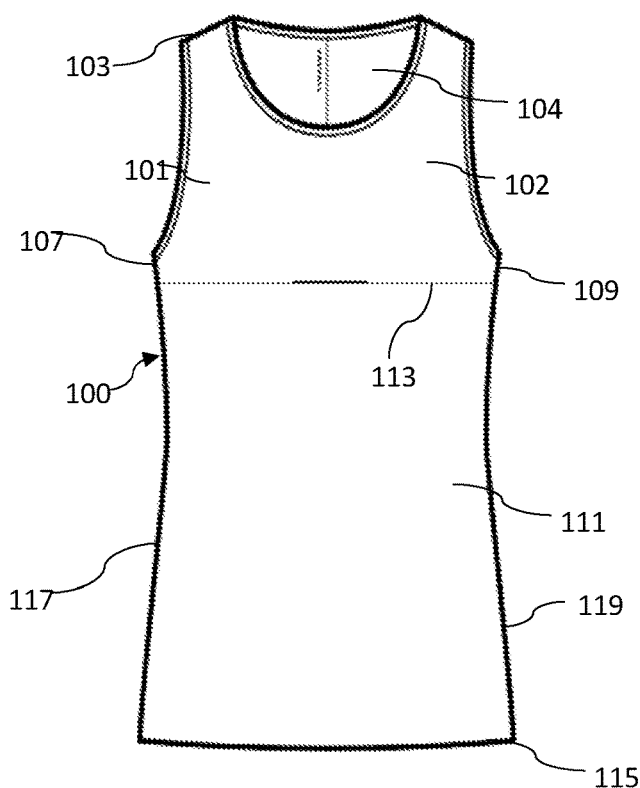
FIG. 2 shows a front surface view of the wearable article of FIG. 1.
Figure 3:
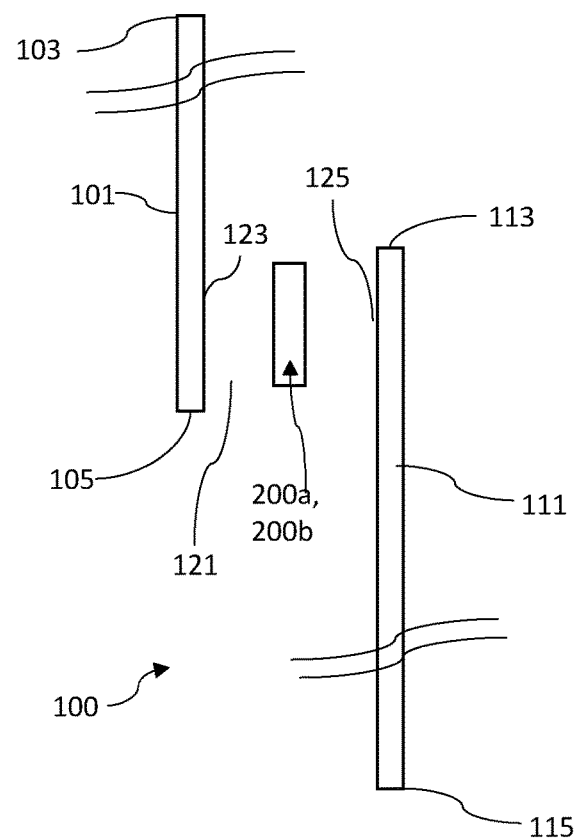
FIG. 3 shows a side exploded view of the wearable article of FIG. 1.

The front section 102 of the wearable article 100 comprises an inner fabric layer 101, also referred to as first portion 101 (FIGS. 1 to 3). The first portion 101 is an upper portion 101 that covers an upper torso region of the front of the wearer when worn. The first portion 101 has a first margin 103 which is an upper margin 103. The upper margin 103 is formed by a superior edge of the first portion 101. The first portion 101 has a second margin 105 which is a lower margin 105. The lower margin 105 is formed by an inferior edge of the first portion 101. The upper margin 103 and the lower margin 105 oppose one another. The first portion 101 further has third and fourth margins 107, 109. The third and fourth margins 107, 109 are side margins 107, 109 formed by opposed side edges of the first portion 101.

The first portion 101 is a layer of material and may be formed of one or more textile panels (e.g. fabric panels).

The first portion 101 and the second portion 111 have a similar size in this example.

The front section 102 of the wearable article 100 comprises an outer fabric layer 111, also referred to as second portion 111. The second portion 111 is a lower portion 111 that covers a lower torso region of the front of the wearer when worn. The second portion 111 has a first margin 113 which is an upper margin 113. The upper margin 113 is formed by a superior edge of the second portion 111. The second portion 111 has a second margin 115 which is a lower margin 115. The lower margin 115 is formed by an inferior edge of the second portion 111. The upper margin 113 and the lower margin 115 oppose one another. The second portion 111 further has third and fourth margins 117, 119. The third and fourth margins 117, 119 are side margins 117, 119 formed by opposed side edges of the second portion 111. In other words, part of the second portion 111 and not the entirety of the second portion 111 overlaps the first portion 101 in the overlapping region 121. Only part of the second portion 111 forms the overlapping region 121.

The second portion 111 is a layer of material and may be formed of one or more textile panels (e.g. fabric panels).

The first portion 101 and the second portion 111 have a similar size in this example.

The second portion 111 overlaps part of the first portion 101 in an overlapping region 121 bounded by the lower margin 105 of the first portion 101 and the upper margin 113 of the second portion 111. In the overlapping region, the second portion 111 is further from the wearer of the article 100 and is thus referred to as an outer fabric layer 111. The first portion 101 is closer to the wearer of the article 100 and is thus referred to as inner fabric layer 101. The inner fabric layer 101 is a skin facing layer of the wearable article 100. The inner fabric layer 101, at least in the overlapping region 121, is closer to the skin surface of the wearer than the outer fabric layer 111.

The second portion 111 overlaps part of the outer surface 123 of the first portion 101 which faces away from the wearer when worn. The second portion 111 is provided in front of the first portion 101 in the overlapping region 121. In the overlapping region 121, part of the outer surface 123 of the first portion 101 faces part of the inner surface 125 of the second portion 111. The inner surface 125 of the second portion 111 faces towards the wearer when worn. The upper margin 103 of the first portion 101 is provided outside of the overlapping region 121. The lower margin 115 of the second portion 101 is provided outside of the overlapping region 121. In other words, part of the second portion 111 and not the entirety of the second portion 111 overlaps the first portion 101 in the overlapping region 121. Only part of the second portion 111 forms the overlapping region 121.

A pocket space 127 is formed between the first portion 101 and the second portion 111 in the overlapping region 121. The pocket space 127 is smaller than the overlapping region 121 and only occupies part of the overlapping region 121. The pocket space 127 has an upper opening with closed side and bottom edges. The upper opening is accessible from the outside surface of the wearable article 100 via the upper margin 113 of the second portion 111. The closed side and bottom edges are formed by a seam 129 that connects the second portion 111 to the first portion 101 in the overlapping region 121. The pocket space 127 is bounded by the seam 129. The seam 129 affixes the upper margin 113 of the second portion 111 to the first portion 101 except for in the region of the pocket space 127. In the region of the pocket space 127, the upper margin 113 of the second portion 111 is unaffixed to the first portion 101. In the region of the pocket space 127, the seam 129 has an approximate U-shape to form the closed side and bottom edges of the pocket space 127.

The first and second portions 101, 111 are not required to be joined to one another at the edges/margins. Other forms of attachment that form an accessible pocket space 127 are within the scope of the present disclosure. For example, the entirety of the second portion 111 may be bonded to the first portion 101 in the overlapping region 121 except for in the vicinity of the pocket space 127.

The pocket space 127 is in a central region between the third margins 107, 117 and the fourth margins 109, 119. The pocket space 127 is in a central area of the wearable article 100 between the upper margin 103 of the first portion 101 and the lower margin 115 of the second portion 111. The pocket space 127 is provided spaced apart from the upper margin of the first portion 101 and the lower margin 115 of the second portion 111. In this example, the pocket space 127 is in an area corresponding to a central torso region of the wearer when worn. This is particularly beneficial for wearable articles 100 incorporating sensing components as it reduces the required length of conductive pathways extending from electrodes in the wearable article 100 to the pocket space 127. Of course, the pocket space 127 may be provided in a different location if desired.

The overlapping region 121 extends from the third margins 107, 117 to the fourth margins 109, 119 of the first and second portions 101, 111. The seam 129 extends from the third margins 107, 117 to the fourth margins 109, 119 of the first and second portions 101, 111 in the overlapping region 121. The seam 129 may be referred to as a horizontal seam as it extends generally in a horizontal direction.

The seam 129 may be a bonded seam. Bonded seams generally refer to double-sided adhesive tapes that can be used to join two pieces of fabric together. Heat and/or pressure may need to be applied to activate the adhesive. The seam 129 may be formed by stitching the second portion 111 to the first portion 101. Other forms of seam are within the scope of the present disclosure. The seam chosen will depend on, amongst other factors, the fabric material of the first and second portions 101, 111.

The second portion 111 is attached to the first portion 101 by seams 131, 133. The seams 131, 133 may be referred to as vertical or side seams as they extend in the vertical direction. The seam 131 joins the third margin 107 of the first portion 101 to the third margin 117 of the second portion 111 in the overlapping region 121. The seam 133 joins the fourth margin 109 of the first portion 101 to the fourth margin 119 of the second portion 111 in the overlapping region 121.

The seams 131, 133 may be bonded seams. The seam 131, 133 may be formed by stitching the second portion 111 to the first portion 101. Other forms of seam are within the scope of the present disclosure. The seam chosen will depend on, amongst other factors, the fabric material of the first and second portions 101, 111. Rather than side seams, the seams 131, 133 may be panel seams 131, 133 or any other form of seam.

The overlapping region 121 is a relatively narrow strip that extends from the third margins 107, 117 of the first and second portions 101, 111 to the fourth margins 109, 119 of the first and second portions 101, 111. The amount of overlap and thus the size of the overlapping region may depend on factors such as the size of the desired pocket space 127.

Advantageously, the wearable article 100 provides a pocket space 127 that is accessible from an outside surface of the article 100 but is not easily visually discernible from the outside surface. The pocket space 127 is hidden within the wearable article 100 and is not visually apparent from outside. The only major visual element is horizontal seam line formed by joining the upper margin 113 of the second portion 111 to the first portion 101. The lower margin 105 of the first portion 101 is hidden within the wearable article 100 and not visually apparent from outside the wearable article 100. Having a hidden pocket space 127 not only provides a wearable article 100 that is more visually attractive, the hidden pocket space 127 provides a mechanism for securely storing potentially valuable items on the person. The wearable article 100 reduces the likelihood of theft by minimising the visual appearance of the pocket space 127 from outside the article. Moreover, the wearable article 100 provides a simplified construction for forming the pocket space 127 meaning that the wearable article 100 can be constructed using established manufacturing techniques and using a limited number of components.

The pocket space 127 construction according to the present disclosure can be incorporated into any form of garment. That is, the front panel of any garment may be provided with the split construction of first and second portions 101, 111 that overlap to define the pocket space 127. A specialist construction of the garment, such as by providing an elasticated band to form the pocket space is not required. The pocket space 127 construction requires a limited number of components and does not require specialist manufacturing techniques. Moreover, the first and second portions 101, 111 can be attached to one another using any form of seam including bonded and stitched seams and are not limited to any particular fabric material.

The wearable article 100 further comprises a plurality (two in this example) of sensing components 200a, 200b. The sensing components 200a, 200b are disposed in the overlapping region 121 between the inner fabric layer 101 and the outer fabric layer 111. The present disclosure is not limited to sensing components and other electronics components are within the scope of the present disclosure.

The sensing components 200a, 200b are adhesive attached to the first portion 101 by adhesive layer 145. The sensing components 200a, 200b have an inner surface 203 that face the first portion 101 and an outer surface 205 that faces away from first portion 101 towards the second portion 111.

The pocket space 127 is sized to receive an electronics module 300. When positioned in the pocket space 127, the electronics module 300 is brought into communication with the sensing components 200a, 200b. This enables the electronics module 300 to send/receive signals from the sensing components 200a, 200b, process signals received from the sensing components 200a, 200b and communicate said processed signals to an external device.

The sensing components 200a, 200b (FIGS. 4 to 5) comprise a base component 201. The base component 201 is a non-conductive fabric layer. The base component 201 may be knitted or woven from non-conductive yarn. The base component 201 has an inner surface 203 and an outer surface 205 opposing the inner surface 203.

The sensing components 200a, 200b comprise conductive regions 209a, 209b, 211a, 211b, 213a, 213b formed of conductive yarn which is integrally knit or woven with the base component 201 to form a sensing component 200a, 200b of an integral construction. That is the sensing component 200a, 200b is formed from a continuous body of fabric. In this example, Circuitex™ conductive yarn from Noble Biomaterials Limited is used to form the conductive regions. Of course, other conductive yarns may be used. The conductive yarn may be a stainless-steel yarn. The conductive yarn may comprise a non-conductive or less conductive base yarn which is coated or embedded with conductive material such as carbon, copper, and silver.

The sensing component 200a, 200b comprises a first conductive region 209a, 209b provided on the first surface 203 of the base component 201. The first conductive region 209a, 209b forms a raised section of conductive material 209, 209a, 209b that extends away from the first surface 203. This raised section of conductive material 209a, 209b forms a raised electrode 209a, 209b for contacting the skin surface of the wearer to measure signals from the wearer and/or introduce signals into the wearer. Having a raised electrode 209a, 209b is beneficial in improving electrode contact with the skin surface particularly when the wearer is moving.

The electrode 209a, 209b may be arranged to measure one or more biosignals of a user wearing the article 100. Here, "biosignal" may refer to any signal in a living being that can be measured and monitored. The electrode 209a, 209b is generally for performing bioelectrical or bioimpedance measurements. Bioelectrical measurements include electrocardiograms (ECG), electrogastrograms (EGG), electroencephalograms (EEG), and electromyography (EMG). Bioimpedance measurements include plethysmography (e.g., for respiration), body composition (e.g., hydration, fat, etc.), and electroimpedance tomography (EIT). The electrode 209a, 209b may additionally or separately be used to apply an electrical signal to the wearer. This may be used in medical treatment or therapy applications.

The first portion 101 comprises openings 143a, 143b aligned with the electrodes 209a, 209b. This means that the electrodes 209a, 209b are not covered by the inner fabric layer 101 and are able to face towards and contact the skin surface of the wearer when the article 100 is worn. The adhesive layer 145 also comprises openings 147a, 147b so that they do not cover the electrodes 209a, 209b.

The sensing component 200a, 200b further comprises a second conductive region 211a, 211b (FIGS. 4 to 5) provided on the second surface 205 of the base component 201. The second conductive region 211a, 211b forms a connection terminal 211a, 211b for electrically connecting with an electronics module 300. The second conductive region 211a, 211b forms a raised conductive region 211a, 211b that extends away from the second surface 205. Having a raised connection terminal 211a, 211b is beneficial in terms of improving the electrical connection between the connection terminal 211a, 211b and the electronics module 300.

The wearable article 100 further comprises waterproof layer 142 (FIG. 1) that is attached to the sensing components 200a, 200b by adhesive layer 144. The waterproof layer 142 is formed from a waterproof film of material. The waterproof layer 142 and adhesive layer 144 have recesses in the vicinity of the pocket space 127. The recesses extend through the waterproof layer 142. The recesses are aligned with the connection terminals 211a, 211b of the sensing component 200a, 200b such that when an electronics module 300 is positioned in the pocket space 127, the electronics module 300 is brought into communication with the connection terminals 211a, 211b. The connection terminals 211a, 211b are aligned with the recesses in the waterproof layer 142 and extend partially into the recesses.

The sensing component 200a, 200b further comprises a conductive pathway 213a, 213b (FIGS. 4 to 5) of conductive material extending from the raised electrode 209a, 209b to the connection terminal 211a, 211b. The conductive pathway 213a, 213b electrically connects the raised electrode 209a, 209b to the connection terminal 211a, 211b. The conductive pathway 213a, 213b is formed of conductive yarn which is knitted or woven into the first surface 203 of the base component 201.

The conductive pathway 213a, 213b is incorporated into the base component 201 and is thus flush with the base component 201. In some examples, the conductive pathway 213a, 213b extends along the inner or outer surface 203, 205. Having a conductive pathway 213a, 213b which is flush with or minimally extends from a surface 203, 205 of the base component 201 is beneficial in terms of improving comfort and minimising the visual appearance of the sensing component 200a, 200b on the wearable article 100.

The first portion 101 covers the conductive pathways 113a, 113b of the sensing components 200a, 200b. This first portion 101 insulates the conductive pathways 113a, 113b and prevents them from contacting a skin surface of the wearer. Advantageously, the wearable article 100 construction sandwiches the sensing components 200a, 200b between inner and outer fabric layers 101, 111 to shield parts of the sensing components 200a, 200b from contact with the wearer's skin. Separate insulating layers are not required and instead the fabric layers of the wearable article perform the shielding function. An insulating layer does not need to be applied to a skin facing surface of the inner fabric layer 101 for example. Moreover, the inner fabric layer 101 is constructed to enabled part of the sensing component 200a, 200b and, in particular, the electrodes 209a, 209b to be exposed to perform their measurement function.

The sensing component 200a, 200b may further comprise a gripper component 215. The gripper component 215 is arranged to grip the sensing component 200a, 200b to the skin surface and hold it in place even when the wearer is moving.

The electronics module 300 is seated on the first portion 101. The electronics module 300 is not permanently attached to the first portion 101 and may be removed and repositioned on the first portion 101 as desired.

Figure 4:
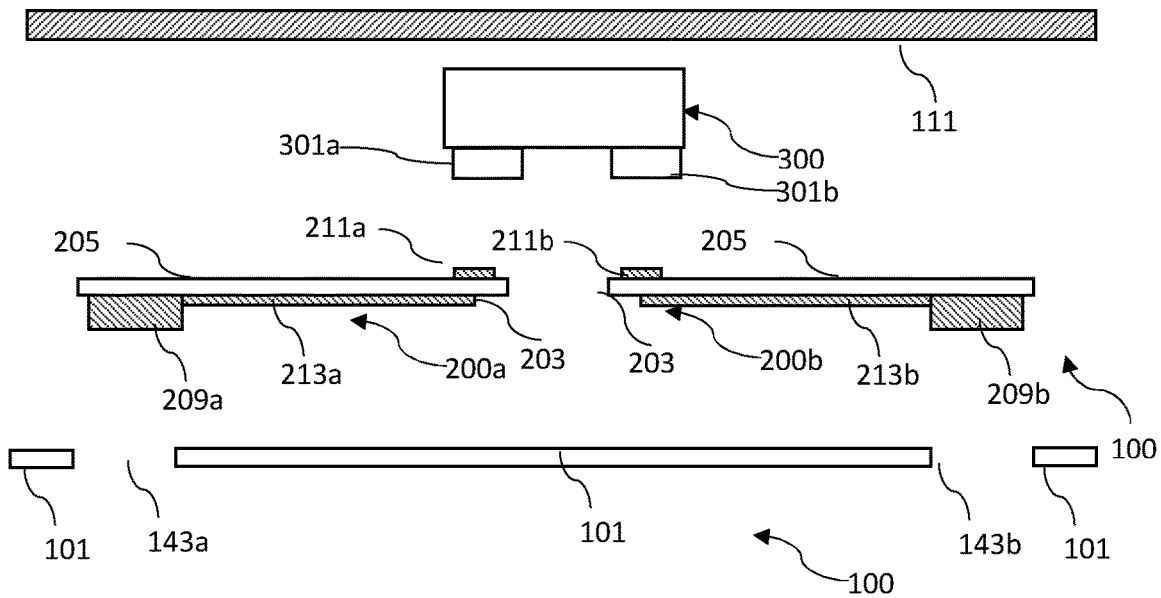
FIG. 4 shows a simplified exploded view of the wearable article of FIG. 1.
Figure 5:
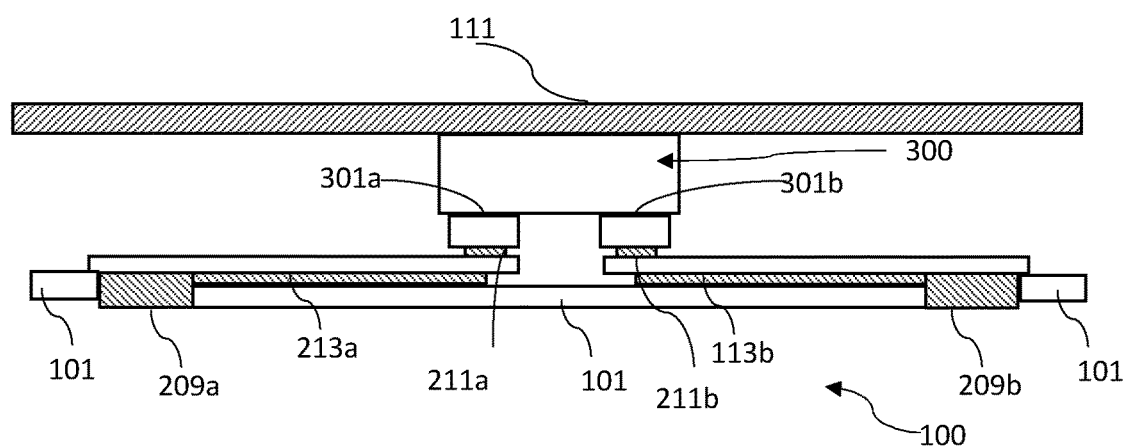
FIG. 5 shows an assembled view of the wearable article of FIG. 4.

When the electronics module 300 is seated on the first portion 101, the conductive pads 301a, 301b of the electronics module 300 contact the connection terminals 211a, 211b of the sensing components 200a, 200b (FIGS. 4 and 5). In this way, the electronics module 300 is electrically connected to the sensing components 200a, 200b and can receive signals from the electrodes 209a, 209b.

The second portion 111 (FIGS. 4 and 5) acts as an attachment mechanism that applies pressure to the electronics module 300 to urge the electronics module 300 towards the first portion 101. In particular, the second portion 101 comprises an elastomeric material that applies pressure to the electronics module 300. Beneficially, the second portion 111 helps restrict movement of the electronics module 300 away from the first portion 101. This helps prevent the conductive pads 301a, 301b from moving out of contact with the connection terminals 211a, 211b.

The example of FIGS. 1 to 5 provides a wearable article 100 that is able to measure biosignals of the wearer via sensing components 200a, 200b and removable electronics module 300 that can be removably positioned in the pocket space 127 to communicatively couple with the sensing components 200a, 200b. Beneficially, the construction of the wearable article 100 minimises/hides the appearance of the pocket space 127 from the outside of the wearable article 100. In this way, the wearable article 100 may appear like a normal garment while still providing the desired monitoring of biosignals for the wearer.

In some example applications such as for EMG, for example, the conductive pathways could be shorter if the pocket space 127 was closer to the muscles which are not at the centre of the wearable article 100. Multiple pocket spaces 127 may be provided on the garment to service multiple EMG sensors required to cover the body. The pocket space 127 could house hardware that is permanently in the wearable article 100 rather than providing a connection to a separate, removable, hardware. The hardware may transmit wirelessly.

Figure 6:
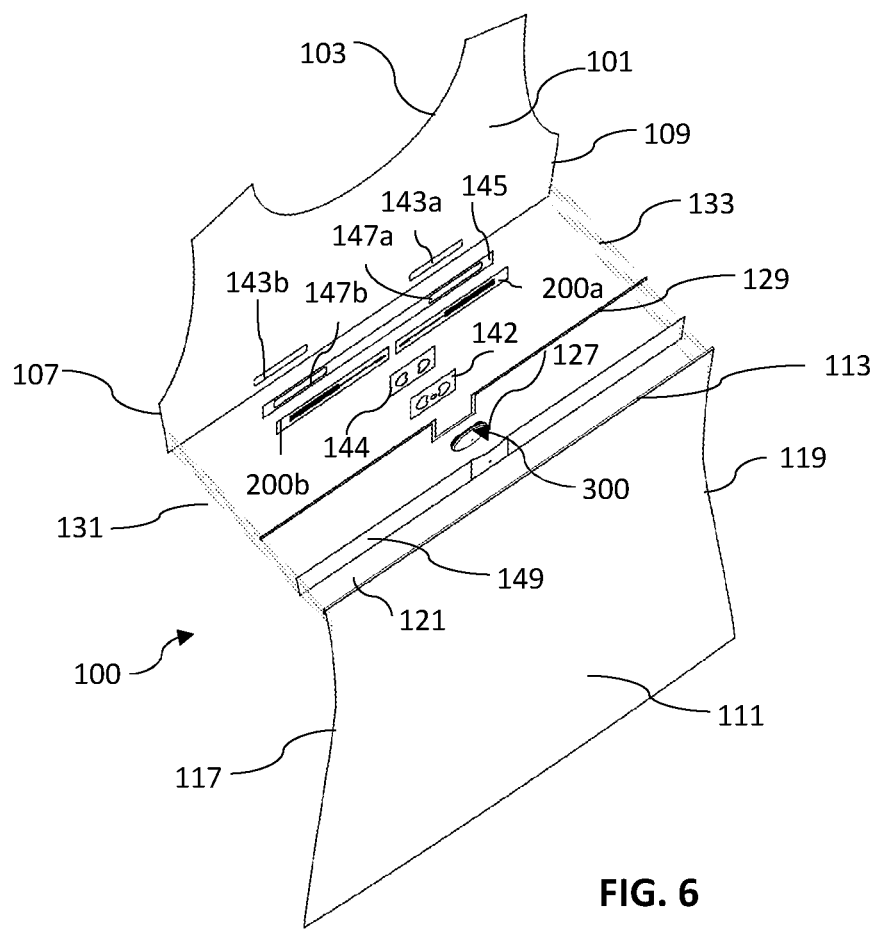
FIG. 6 shows an exploded front surface view of yet another example wearable article according to aspects of the present disclosure.

Referring to FIG. 6, there is shown another example wearable article 100 according to aspects of the present disclosure. The wearable article 100 has a similar construction to the wearable article of the preceding figures and like reference numerals are used to indicate like components.

The wearable article 100 further comprises a third portion 149. The third portion 149 is disposed between the first and second portions 101, 111 in the overlapping region 121. The third portion 149 is a narrow strip of material with similar dimensions to the overlapping region 121 such that the third portion 149 is contained within the overlapping region 121 and does not extend outside of the overlapping region. The third portion 149 extends from the third margins 107, 117 of the first and second portions 101, 111 to the fourth margins 109, 119 of the first and second portions 101, 111. The third portion 149 is a middle fabric layer. The third portion 149 is not required to extend for the complete length of the overlapping region. The third portion 149 may be sized to be slightly larger than the pocket space 127.

The third portion 149 is attached to the first portion 101 in the overlapping region 121 by the horizontal seam 129. The second portion 111 is attached to the first portion 101 by the side seams 131, 133 only.

The pocket space 127 is formed between the first portion 101 and the third portion 149 in the overlapping region 121. The second portion 111 covers the third portion 149 and thus further minimises the appearance of the pocket space 127 from the external surface of the wearable article 100. The second portion 111 may minimise the appearance of the horizontal seam 129 from outside of the wearable article 100. Moreover, by creating the pocket space 127 from panels 101 and 149, they become the weight bearing structures for the electronics module 300 in the overlapping region121 where they are hidden from external view. he visible part of panel 101 and panel 111 are free from impact from the electronics module 300.

The third portion 149 acts as an attachment mechanism that applies pressure to the electronics module 300 to urge the electronics module 300 towards the surface 123 of the first portion 101. The third portion 149 may be comprise an elastomeric material to enable this function. The third portion 149 may perform this function alone or in combination with the second portion 111.

Figure 7:
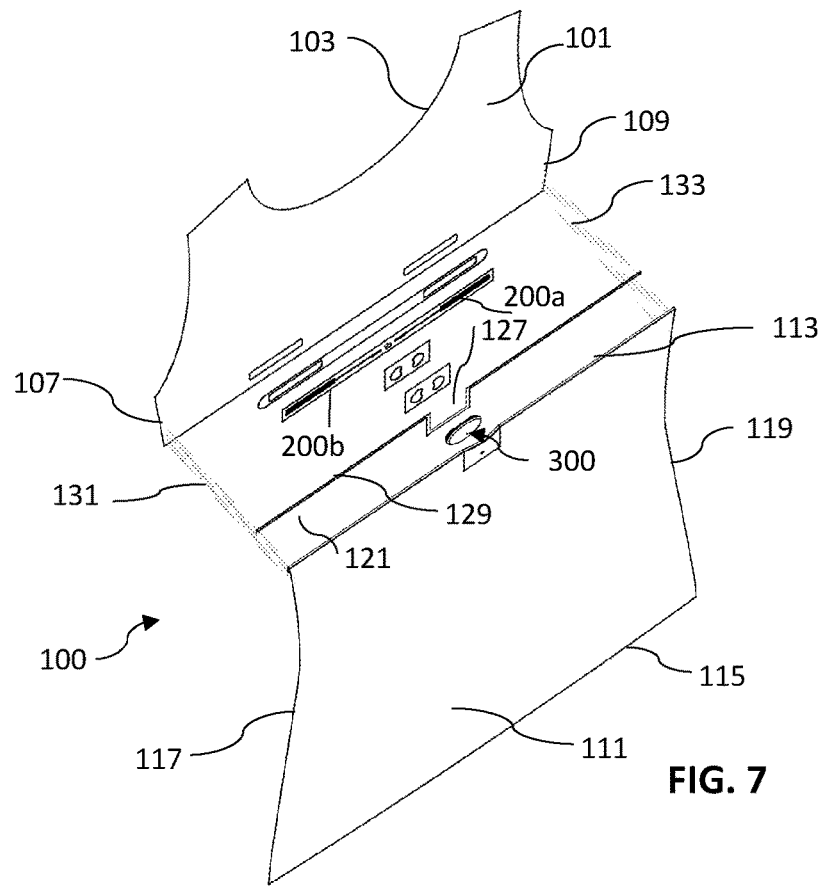
FIG. 7 shows an exploded front surface view of yet another example wearable article according to aspects of the present disclosure.

Referring to FIG. 7, there is shown another example wearable article 100 according to aspects of the present disclosure. The wearable article 100 has a similar construction to the wearable article of the preceding figures and like reference numerals are used to indicate like components. In this example, the sensing components 200a, 200b are not provided as separate articles but instead are provided as a single article. That is, the sensing components 200a, 200b share a common base layer 201.

Figure 8:
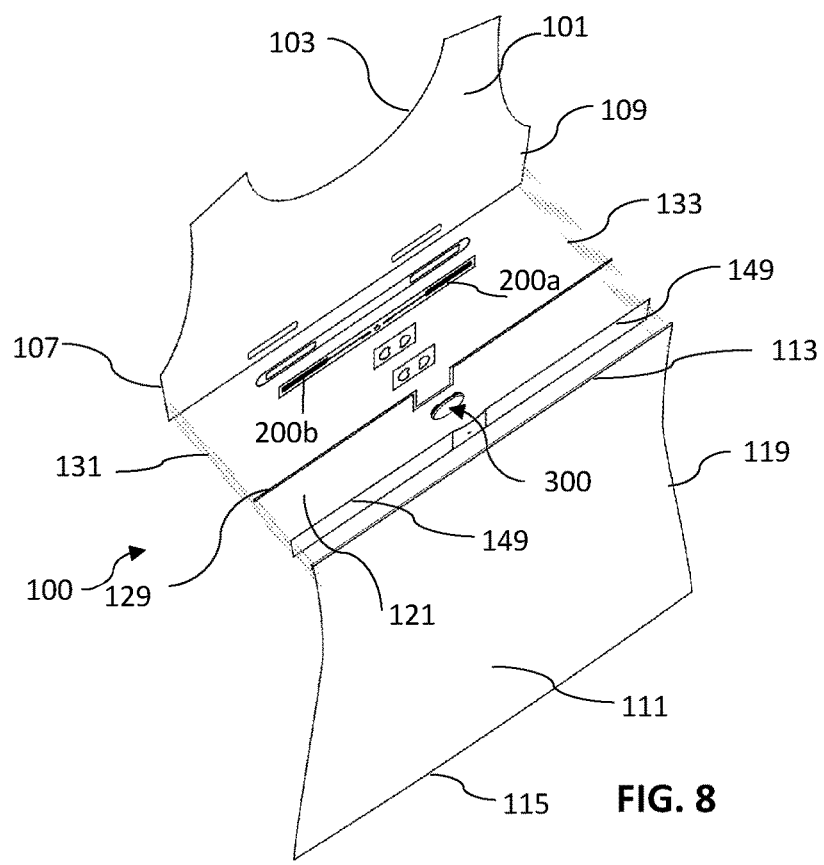
FIG. 8 shows an exploded front surface view of yet another example wearable article according to aspects of the present disclosure.

Referring to FIG. 8, there is shown another example wearable article 100 according to aspects of the present disclosure. The wearable article 100 has a similar construction to the wearable article of the preceding figures and like reference numerals are used to indicate like components. In this example, the sensing components 200a, 200b are not provided as separate articles but instead are provides as a single article. A third portion 149 is provided between the first portion 101 and the second portion 111 in the overlapping region 121.

Figure 9:
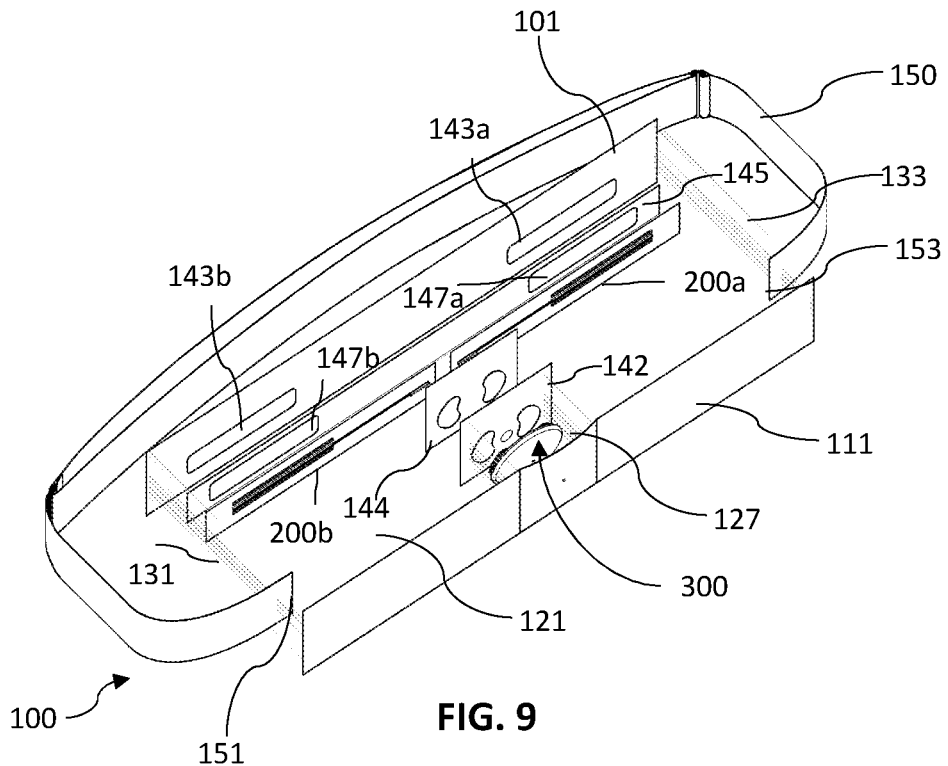
FIG. 9 shows an exploded view of yet another example wearable article according to aspects of the present disclosure.

Referring to FIG. 9, there is shown another example wearable article 100 according to aspects of the present disclosure. The wearable article 100 has a similar construction to the wearable article of the preceding figures and like reference numerals are used to indicate like components.

The outer fabric layer 111 has similar dimensions to the inner fabric layer 101. The overlapping region 121 is formed between the upper margins of the inner and outer fabric layer 101, 111 and the lower margins of the inner and outer fabric layer 101, 111.

The wearable article 100 comprises a strip of material 150 that is attached to the inner and outer layers 101, 111 to form a strap 100 arranged to surround a circumference of the wearer. The strap 150 in this example is chest strap 100 for surrounding the torso of the wearer. The strip of material 150 has a first end 151 that is joined between the inner and outer fabric layers by side seam 131. The strip of material 150 further has a second end 153 joined to the inner and outer fabric layers 101, 111 by the side seam 133. The first end 151 and second end 153 are therefore attached to opposed side margins of the inner and outer fabric layers 100, 111.

A pocket space 127 is defined between the first end 151 and the second end 153 of the strip of material 150. The pocket space 127 formed by attaching the outer layer 111 to the side edges of the waterproof layer 142.

Figure 10:
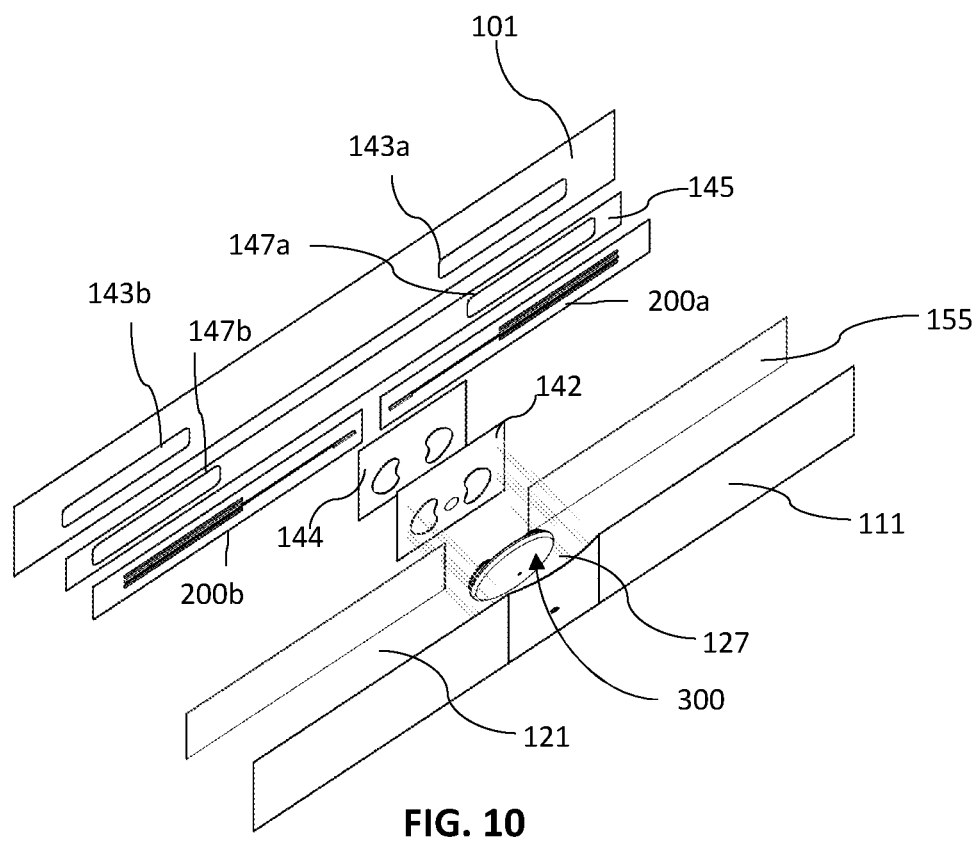
FIG. 10 shows an exploded front surface view of yet another example wearable article according to aspects of the present disclosure.

Referring to FIG. 10, there is shown another wearable article 100 according to aspects of the present disclosure. The wearable article 100 has a similar construction to the wearable article of the preceding figures and like reference numerals are used to indicate like components.

The wearable article 100 comprises a band formed from the outer and inner fabric layers 101, 111. The band 101, 111 is arranged to surround a circumference of the wearer when worn. The band 101, 111 may be a waist band arranged to extend around the waist of the wearer. The band 101, 111 may be an arm band arranged to extend around the arm of the wearer. The band 101, 111 may be a chest band arranged to extend around the chest of the wearer. The band 101, 111 may be an underband of a bra.

The outer fabric layer 111 has similar dimensions to the inner fabric layer 101.

The wearable article 100 comprises a stretch layer 155 of elastomeric material is provided between the outer and inner fabric layers 101, 111. The stretch layer 155 is arranged to tension the wearable article 100 when worn. The stretch layer 155 provides a gap in the pocket space 127. The stretch layer 155 defines an open region in the pocket space 127 for receiving the electronics module 300.

The elastomeric material 155 defines an open region in the pocket space 127 formed between the inner and outer fabric layers 101, 111. In this way, the elastomeric material 155 does not affect the communication between the electronics module 300 and the connection terminals 211a, 211b when the electronics module 300 is positioned in the pocket space.

The elastomeric material 155 is a continuous strip of material that comprises a first end and a second end. The first end and the second end are spaced apart from one another to define the open region. That is, the first end and the second end of the elastomeric material 155 are not connected to one another.

Advantageously, the elastomeric material provides tensioning for the wearable article while still providing an open region in the pocket space for receiving the electronics module. This means that the elastomeric material does not affect the placement of the electronics module in the pocket space and does not affect any connections formed between the electronics module and other components of the wearable article.

Figure 11:
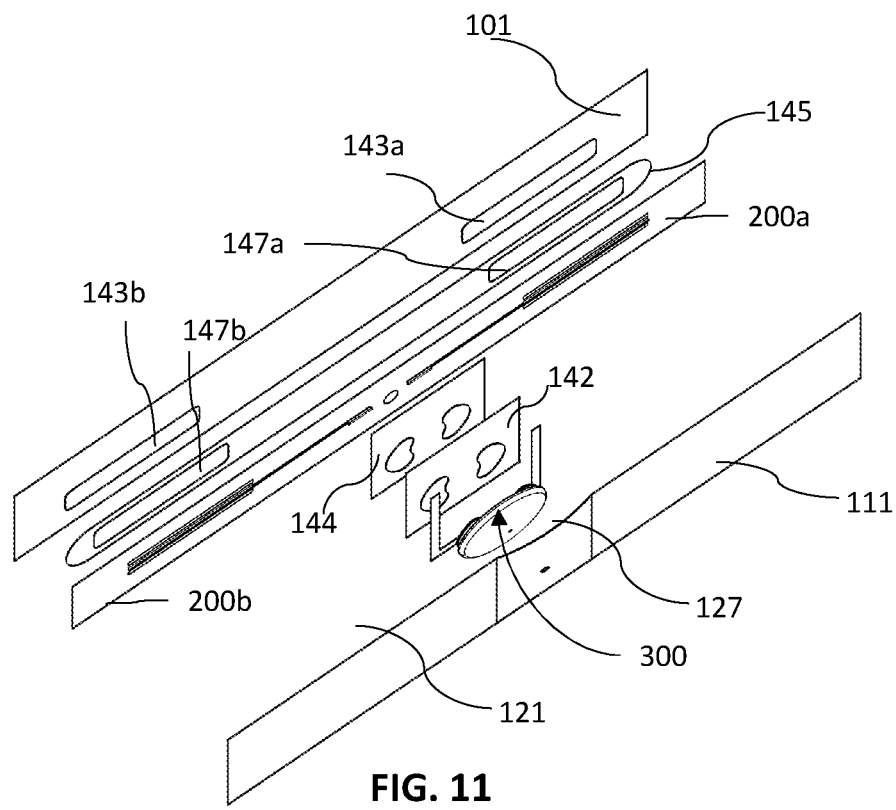
FIG. 11 shows an exploded front surface view of yet another example wearable article according to aspects of the present disclosure.

Referring to FIG. 11, there is shown another example wearable article 100 according to aspects of the present disclosure. The wearable article 100 has a similar construction to the wearable article of the preceding figures and like reference numerals are used to indicate like components. In this example, the sensing components 200a, 200b are incorporated into the stretch layer 155. This provides a simpler construction with fewer components.

Figure 12:
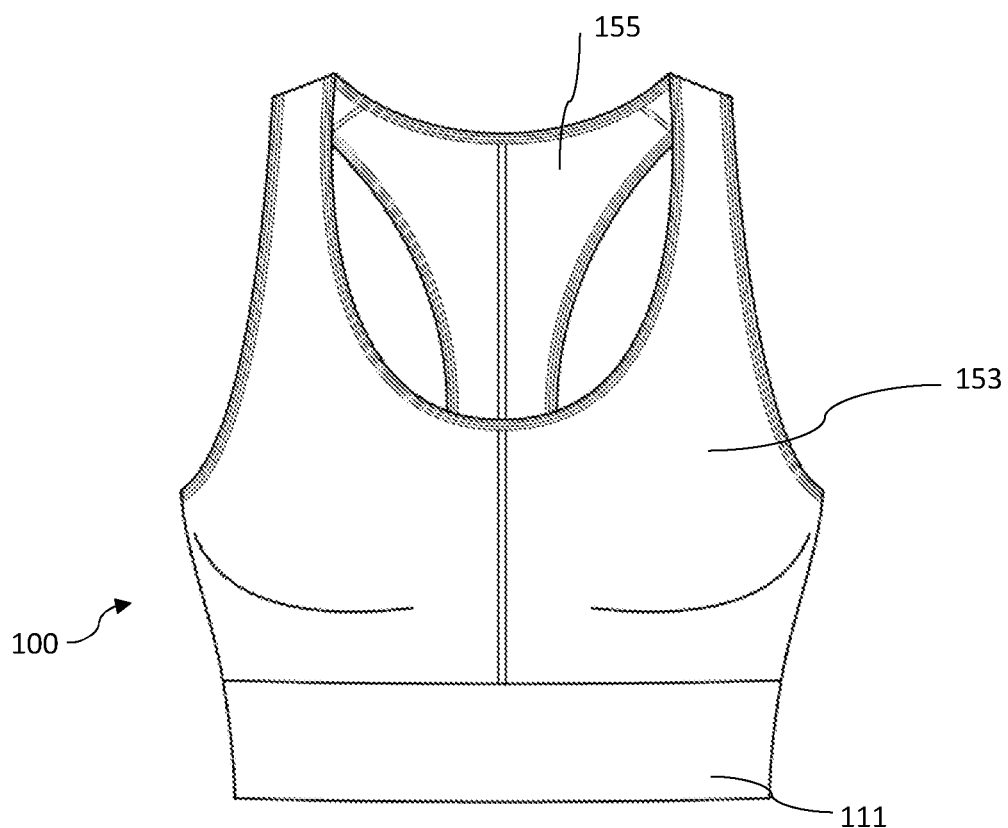
FIG. 12 a front surface view of yet another example wearable article according to aspects of the present disclosure.

Referring to FIG. 12, there is shown another example wearable article 100 according to aspects of the present disclosure. The wearable article 100 has a similar construction to the wearable article of the preceding figures and like reference numerals are used to indicate like components.

The wearable article 100 is in the form of a bra. The bra 100 comprises a front portion 153, inner portion 155 and underband portion 101, 111 extending from a lower margin of the front portion 153 and the back portion 155 of the bra 100. The underband portion 101, 111 comprises the inner fabric layer 101 and the outer fabric layer 111. The underband portion 101, 111 may be the band of FIG. 10 or FIG. 11. The underband 101, 111 surrounds the circumference of the wearer of the wearable article 100. The pocket space 127 is formed in a central front region of the bra underband 101, 111. The pocket opening 127 is provided at the top of the underband to allow for the electronics module 300 to be inserted into and removed from the pocket space.

Figure 13:
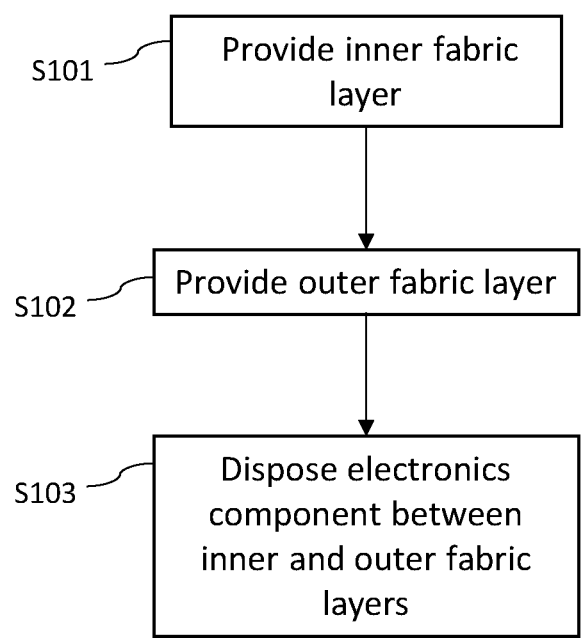
FIG. 13 a flow diagram for an example method of making an article according to aspects of the present disclosure.

Referring to FIG. 13, there is shown a method of manufacturing a wearable article according to aspects of the present disclosure.

Step S101 comprises providing an inner fabric layer.

Step S102 comprises providing an outer fabric layer overlapping the inner fabric layer to form an overlapping region.

Step S103 comprises disposing an electronics component between the inner and outer fabric layer in the overlapping region, wherein the inner fabric layer comprises an opening to expose at least part of the electronics component.

The method may comprise attaching the second portion to the first portion to form the overlapping region. This may comprise attaching the third margins of the first and second portion together in the vicinity of the overlapping region. This may comprise attaching the fourth margins of the first and second portion together in the vicinity of the overlapping region. This may comprise attaching the upper margin of the second portion to the first portion except for in the region of the pocket space.

The method may comprise providing a third portion having first and second opposed margins.

The method may comprise attaching the third portion to the first portion to form the pocket space. The third portion may be disposed in the overlapping region between the first and second portions.

In one example method of construction referring to the wearable article 100 of FIG. 1, for example, the adhesive layer 145 and sensing components 200*a*, 200*b* may be attached to the first portion 101 by bonding. The waterproof layer 142 and the adhesive layer 144 may be attached to the second portion 101 by stitching. The first portion 101 may then be attached to the second portion 111 by bonding or stitching.

During an example manufacturing process, the second portion may be attached to the first portion to form the front panel (front surface 102, FIG. 4) of the wearable article. The front panel may then be attached to rear panel (back surface 104, FIG. 4) to form the finished wearable article. The construction of the front panel may take place at a first location/factory and the joining of the front panel to the back panel may take place at a second location/factory. Advantageously, the front panel potentially incorporating electronics components can be manufactured at a first location, the assembled first panel can be transported to a general garment manufacture for final assembly.

While the above examples refer generally to sensing components 200*a*, 200*b* formed using knitting and weaving techniques the present disclosure is not limited to these examples. The sensing components 200*a*, 200*b* can comprise any desired conductive material and are not limited to knitted and woven conductive yarns. The conductive material may include printed conductive ink or conductive transfers formed from layers of insulating and conductive ink. Other forms of conductive material that can be incorporated onto a fabric are within the scope of the present disclosure. The sensing components 200*a*, 200*b* in some examples may be integral with the first portion 101.

Some or all the adhesive layers 144, 145 may not be required in all examples of the wearable article 100. Some components may have integral adhesive meaning that separate adhesive layers are not required. A different method of joining components together such as through stitching may be provided so that an adhesive is not required. In some examples, components may be integrally formed with one another such that an adhesive is not necessary.

The waterproof layer 142 is not required in all examples of the wearable article 100. The first portion 101 may be waterproof at least in the section adjacent to the pocket space. In addition, the electronics module 300 may be constructed in a way that avoids the need for separate waterproofing.

The electronics module 300 is not required to contact the connection terminals 211*a*, 211*b* to communicate with the sensing component 200*a*, 200*b*. For example, the sensing component 200*a*, 200*b* and the electronics module 300 may wirelessly communicate by forming an inductive coupling. The sensing component 200*a*, 200*b* and the electronics module 300 may both comprise an antenna for forming the inductive coupling. In these examples, the interface element 301 of the electronics module 300 is not required to be conductive and may be a non-conductive locating mechanism although it still may be in the form of one or more pads.

Two separate sensing components 200*a*, 200*b* are not required in all aspects of the present disclosure. The sensing components 200*a*, 200*b* may be connected together. A single sensing component may be provided comprising any number of connection terminals and electrodes or other sensing circuitry.

The attachment mechanism does not need to be formed by the second portion 111 or third portion 149. Other forms of attachment such as magnetic attachment may separately or additionally be provided.

A magnetic material (magnet) may be attached to the waterproof layer 142 or other layer of the wearable article 100 such as the sensing components 200*a*, 200*b*. The magnet provides an attachment mechanism for coupling the electronics module 300 to the wearable article 100 when the electronics module 300 is positioned in the pocket space 127. The magnet may be incorporated directly into a material layer of the wearable article, may be stitched to the layer, or may be housed in a pocket formed by the layer. The magnet may be first encapsulated in a plastic film which is then stitched to the layer. The magnet may be provided between the connection terminals 211*a*, 211*b* of the sensing components 200*a*, 200*b* such as by being positioned between the recesses in the waterproof layer 142.

The first portion 101 is not required to be an upper portion. The second portion 111 is not required to be a lower portion. The first portion 101 and the second portion 111 may be left and right-side portions for example. The seam 129 in such an example may extend vertically rather than horizontally. The wearable article 100 is not required to be a sleeveless shirt. Other wearable articles are within the scope of the present disclosure.

Figure 14:
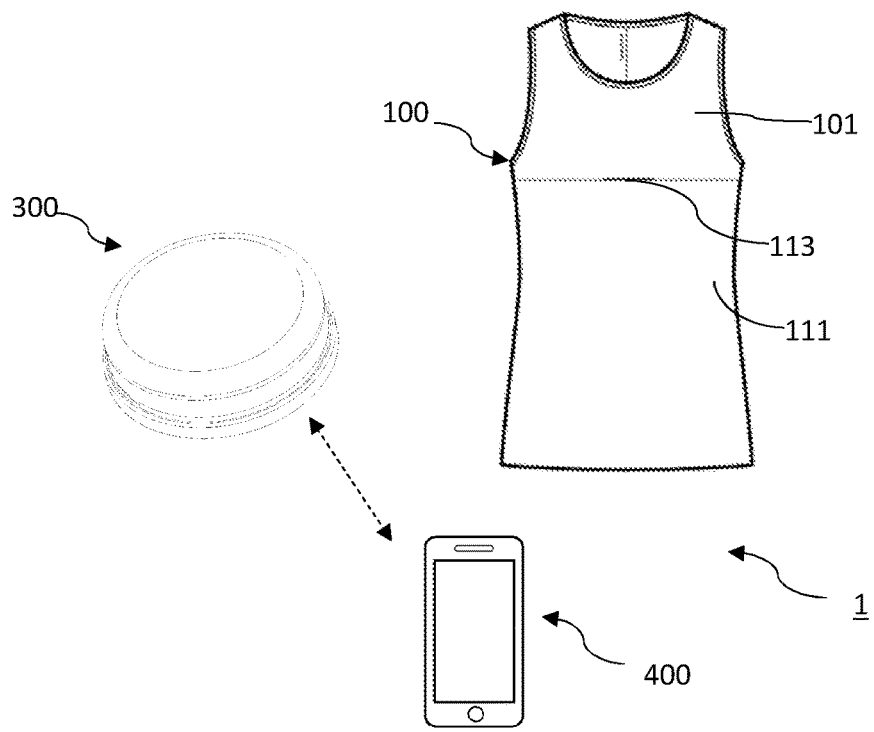
FIG. 14 shows an example system according to aspects of the present disclosure.

Referring to FIG. 14, there is shown an example system 1 according to aspects of the present disclosure. The system 1 comprises a wearable article 100, electronics module 300 and a mobile device 400.

The electronics module 300 can be disposed within the pocket space formed by the first and second portions 101, 111. The pocket space 127 is accessible via the upper margin 113 of the second portion 111. When positioned within the pocket space, the electronics module 300 can integrate with the sensing components to obtain signals from the sensing components. The electronics module 300 is further arranged to wirelessly communicate data to the mobile device 400. Various protocols enable wireless communication between the electronics module 300 and the mobile device 400. Example communication protocols include Bluetooth®, Bluetooth® Low Energy, and near-field communication (NFC).

The present disclosure is not limited to electronics modules 300 that communicate with mobile devices 400 and instead may communicate with any electronic device capable of communicating directly with the electronics module 300 or indirectly via a server over a wired or wireless communication network. The electronic device may be a wireless device or a wired device. The wireless/wired device may be a mobile phone, tablet computer, gaming system, MP3 player, point-of-sale device, or wearable device such as a smart watch. A wireless device is intended to encompass any compatible mobile technology computing device that connects to a wireless communication network, such as mobile phones, mobile equipment, mobile stations, user equipment, cellular phones, smartphones, handsets or the like, wireless dongles or other mobile computing devices. The wireless communication network is intended to encompass any type of wireless network such as mobile/cellular networks used to provide mobile phone services.

Beneficially, the removable electronic module 300 may contain all the components required for data transmission and processing such that the wearable article 100 only comprises the sensing components. In this way, manufacture of the wearable article 100 may be simplified. In addition, it may be easier to clean a wearable article 300 which has fewer electronic components attached thereto or incorporated therein. Furthermore, the removable electronics module 300 may be easier to maintain and/or troubleshoot than embedded electronics. The electronics module 300 may comprise flexible electronics such as a flexible printed circuit (FPC). The electronics module 300 may be configured to be electrically coupled to the wearable article 300.

It may be desirable to avoid direct contact of the electronics module 300 with the wearer's skin while the wearable article 300 is being worn. It may be desirable to avoid the electronics module 300 contacting sweat or moisture on the wearer's skin. The electronics module 300 may be provided with a waterproof coating or waterproof casing. For example, the electronics module 300 may be provided with a silicone casing.

Figure 15:
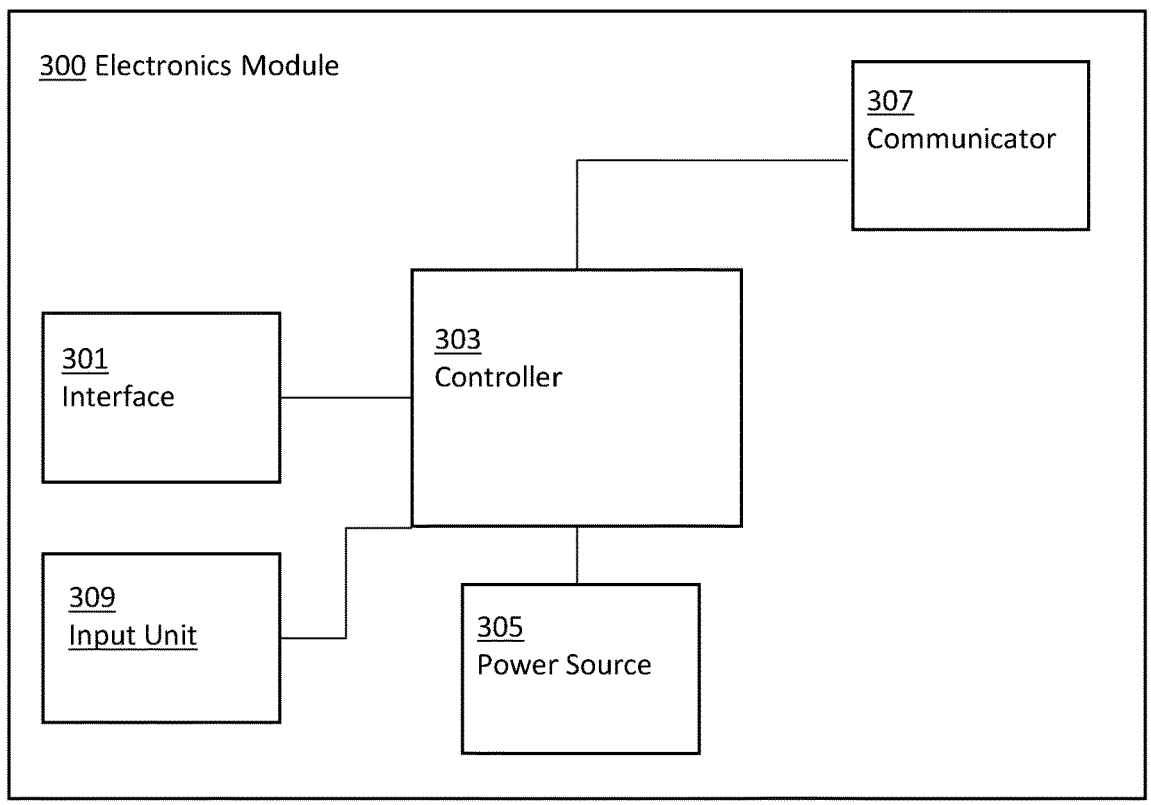
FIG. 15 shows a schematic diagram for an example electronics module according to aspects of the present disclosure.

Referring to FIG. 15, there is shown a schematic diagram of an example of the electronics module 300. The electronics module 300 comprises an interface 301, a controller 303, a power source 305, and a communicator 307.

The interface 301 is arranged to communicatively couple with the sensing component of the fabric article to receive a signal from the sensing component. The controller 303 is communicatively coupled to the interface 301 and is arranged to receive the signals from the interface 301. The interface 301 may form a conductive coupling or a wireless (e.g. inductive) communication coupling in some examples. That is, the connection terminal of the fabric article may be in the form of an antenna for inductively coupling to a corresponding antenna of the interface 301. The interface 301 may comprise conductive pads as described above.

The power source 305 is coupled to the controller 303 and is arranged to supply power to the controller 303. The power source 305 may comprise a plurality of power sources. The power source 105 may be a battery. The battery may be a rechargeable battery. The battery may be a rechargeable battery adapted to be charged wirelessly such as by inductive charging. The power source 305 may comprise an energy harvesting device. The energy harvesting device may be configured to generate electric power signals in response to kinetic events such as kinetic events performed by a wearer of the article. The kinetic event could include walking, running, exercising or respiration of the wearer. The energy harvesting material may comprise a piezoelectric material which generates electricity in response to mechanical deformation of the converter. The energy harvesting device may harvest energy from body heat of a wearer of the article. The energy harvesting device may be a thermoelectric energy harvesting device. The power source may be a super capacitor, or an energy cell.

The communicator 307 may be a mobile/cellular communicator operable to communicate the data wirelessly via one or more base stations. The communicator 307 may provide wireless communication capabilities for the wearable article and enables the wearable article to communicate via one or more wireless communication protocols such as used for communication over: a wireless wide area network (VWVAN), a wireless metroarea network (VVMAN), a wireless local area network (VVLAN), a wireless personal area network (VVPAN), Bluetooth® Low Energy, Bluetooth® Mesh, Bluetooth® 5, Thread, Zigbee, IEEE 802.15.4, Ant, a near field communication (NFC), a Global Navigation Satellite System (GNSS), a cellular communication network, or any other electromagnetic RF communication protocol. The cellular communication network may be a fourth generation (4G) LTE, LTE Advanced (LTE-A), LTE Cat-M1, LTE Cat-M2, NB-IoT, fifth generation (5G), sixth generation (6G), and/or any other present or future developed cellular wireless network. A plurality of communicators may be provided for communicating over a combination of different communication protocols.

The electronics module 300 may comprise a Universal Integrated Circuit Card (UICC) that enables the electronics module 300 to access services provided by a mobile network operator (MNO) or virtual mobile network operator (VMNO). The UICC may include at least a read-only memory (ROM) configured to store an MNO/VMNO profile that the electronics module 300 can utilize to register and interact with an MNO/VMNO. The UICC may be in the form of a Subscriber Identity Module (SIM) card. The electronics module 300 may have a receiving section arranged to receive the SIM card. In other examples, the UICC is embedded directly into the controller 303 of the electronics module 300. That is, the UICC may be an electronic/embedded UICC (eUICC). A eUICC is beneficial as it removes the need to store several MNO profiles, i.e. electronic Subscriber Identity Modules (eSIMs). Moreover, eSIMs can be remotely provisioned to electronics modules 200. The electronics module 300 may comprise a secure element that represents an embedded Universal Integrated Circuit Card (eUICC).

The input unit 309 enables the electronics module 300 to receive a user input for controlling the operation of the electronics module 300. The input unit 309 may be any form of input unit capable of detecting an input event. The input event is typically an object being brought into proximity with the electronics module 300.

In some examples, the input unit 309 comprises a user interface element such as a button. The button may be a mechanical push button.

In some examples, the input unit 309 comprises an antenna. In these examples, the input event is detected by a current being induced in the first antenna. The mobile device 400 is powered to induce a magnetic field in an antenna of the mobile device 400. When the mobile device 400 is placed in the magnetic field of the antenna, the mobile device 400 induces current in the antenna.

In some examples, the input unit 309 comprises a sensor such as a proximity sensor or motion sensor. The sensor may be a motion sensor that is arranged to detect a displacement of the electronics module 300 caused by an object being brought into proximity with the electronics module 300. These displacements of the electronics module 300 may be caused by the object being tapped against the electronics module 300. Physical contact between the object and the electronics module 300 is not required as the electronics module 300 may be in the pocket space 127 of the wearable article 100. This means that there may be a fabric (or other material) barrier between the electronics module 300 and the object. In any event, the object being brought into contact with the fabric of the pocket will cause an impulse to be applied to the electronics module 300 which will be sensed by the sensor.

Figure 16:
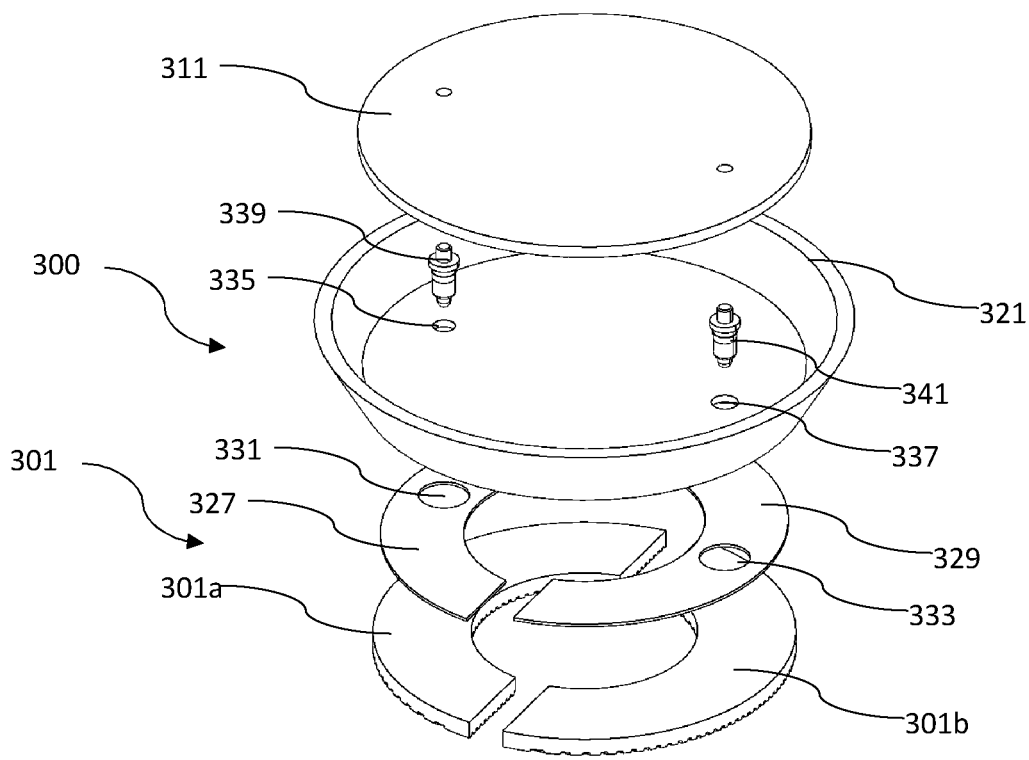
FIG. 16 shows an exploded view of another example electronics module according to aspects of the present disclosure.
Figure 17:
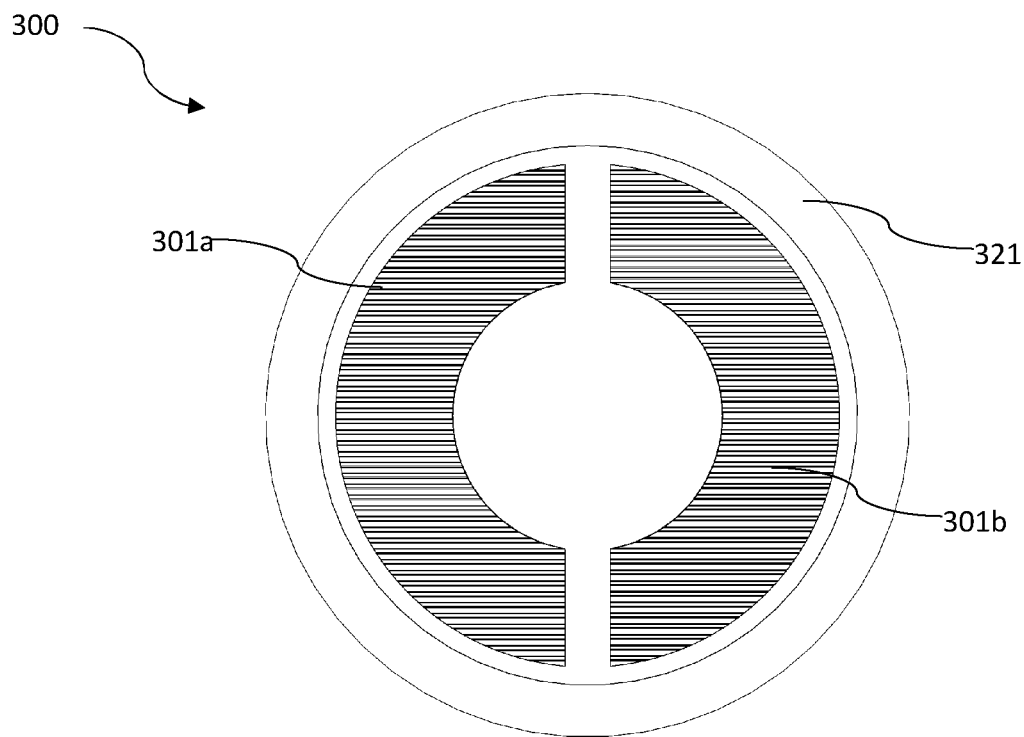
FIG. 17 shows the bottom surface of the electronics module of FIG. 16

Referring to FIGS. 16 and 17, there is shown another example electronics module 300 according to aspects of the present disclosure. The top enclosure 319 is omitted so that the internal components of the electronics module 300 are visible.

The electronics module comprises interface elements 301a, 301b in the form of conductive pads 201a, 201b. The two conductive pads 301a, 301b are adhesively attached to the external surface of the bottom enclosure 321 using adhesive layers 327, 329. The adhesive layers 327, 329 comprise openings 331, 333. These openings 331, 333 are aligned with openings 335, 337 provided in the bottom enclosure 321.

Pogo pins 339, 341 extend through openings 335, 337 in the bottom enclosure 321 and openings 331, 333 in the adhesive layers 327, 329 to electrically connect to the conductive pads 301a, 301b. The openings 331, 333 in the adhesive layers 327, 329 are larger than the openings 335, 337 in the bottom enclosure 321 to help ensure that adhesive does not interfere with the pogo pin mechanism or cause a potential short circuit. The pogo pins 339, 341 electrically connect the printed circuit board 311 to the conductive pads 301a, 301b.

Pogo pins 339, 341 are not required in all examples and other forms of force-biased conductor may be used.

The conductive pads 301a, 301b are formed from conductive elastomeric material 301a, 301b. The conductive elastomeric material used in this example is a conductive silicone rubber material, but other forms of conductive elastomeric material may be used. Beneficially, elastomeric material such as conductive silicone rubber can have an attractive visual appearance and may easily be moulded or extruded to have branded or other visual elements. The pads 301a, 301b may be textured to provide additional grip when positioned on the wearable article 100. The texture may be, for example, a ribbed or knurled texture. The elastomeric material 301a, 301b have a ribbed texture. The conductive pads 301a, 301b are not required to be formed of elastomeric material other conductive materials such as metals or conductive fabric may be used.

The conductive pads 301a, 301b together form a split-ring shape, but other shapes and arrangements are within the scope of the present disclosure.

The housing 319, 321 has a circular cross-sectional shape but this is not required. The housing may have any cross-sectional shape such as oval, square, or rectangular.

In the present disclosure, the electronics module may also be referred to as an electronics device or unit. These terms may be used interchangeably.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. In some embodiments, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive.

Throughout this specification, the term "comprising" or "comprises" means including the component(s) specified but not to the exclusion of the presence of others.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent, or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wearable article comprising:
a first fabric portion comprising a lower margin and an inferior edge of a first fabric layer;
a second fabric portion comprising an upper margin and a superior edge of a second fabric layer;
an overlapping region in which the second fabric layer or the second fabric portion overlaps the first fabric portion including the inferior edge, whereby the first fabric portion forms an inner fabric layer and the second fabric layer or the second fabric portion forms an outer fabric layer;
a seam between the upper margin and the lower margin, said seam having a fixed portion in which the upper margin is fixed to the lower margin, and an unaffixed portion in which the upper margin is not fixed to the lower margin;
a pocket space between the inner fabric layer and the outer fabric layer, said pocket space is defined by the fixed portion and the unaffixed portion forms an opening at the top of the pocket space;
a sensing component disposed at least partially between the inner and outer fabric layer in the overlapping region, the sensing component comprising a non-conductive fabric base component and conductive regions provided on the base component, said conductive regions form an electrode and a conductive pathway; and
an opening in the inner fabric layer, said opening exposes at least part of the electrode,
wherein the sensing component is arranged such that when an electronics module that processes or communicates data is positioned in the pocket space, the electronics module is brought into communication with the sensing component.

2. The wearable article as claimed in claim 1, wherein the inner fabric layer covers the conductive pathway.

3. The wearable article as claimed in claim 1, wherein the outer fabric layer covers the conductive pathway.

4. The wearable article as claimed in claim 1, wherein the sensing component has an outer surface facing the outer fabric layer and an inner surface facing the inner fabric layer.

5. The wearable article as claimed in claim 4, wherein the electrode is provided on the inner surface.

6. The wearable article as claimed in claim 4, wherein the sensing component comprises a connection terminal for connecting with an electronics module, wherein the connection terminal is provided on the outer surface.

7. The wearable article as claimed in claim 1, further comprises a middle fabric layer disposed between the inner and outer fabric layers in the overlapping region, and wherein the pocket space is formed between the inner and middle fabric layers in the overlapping region.

8. The wearable article as claimed in claim 1, wherein an outer layer of the pocket space forms an attachment mechanism for holding the electronics module in communication with the sensing component.

9. The wearable article as claimed in claim 8, wherein the outer layer of the pocket space comprises a stretch material and forms a pressure membrane arranged to apply pressure to the electronics module when located within the pocket space, the pressure urges the electronics module into communication with the sensing component.

10. The wearable article as claimed in claim 1, wherein the pocket space is accessible from an outside surface of the wearable article.

11. The wearable article as claimed in claim 10, wherein the pocket space is accessible from a margin of the outer fabric layer.

12. The wearable article as claimed in claim 1, further comprising a stretch material provided between the outer and inner fabric layers and arranged to tension the wearable article when worn.

13. The wearable article as claims in claim 1, wherein the wearable article comprises a band arranged to surround a circumference of a wearer, wherein the band comprises the outer fabric layer and the inner fabric layer.

14. The wearable article as claimed in claim 13, wherein the wearable article is a bra, and wherein the bra comprises a front portion, a back portion and the band comprising the outer and inner fabric layers, wherein the band forms an underband portion extending from a lower margin of the front portion and the back portion of the bra.

15. The wearable article as claimed in claim 1, wherein the overlapping region extends between side margins of the upper and lower portions.

16. The wearable article as claimed in claim 1, wherein the wearable article is a top.

17. The wearable article as claimed in claim 1, wherein the conductive regions are integrally knit or woven with the base component.

18. The wearable article as claimed in claim 1, wherein the sensing component is attached to the inner fabric layer.

19. An assembly comprising an electronics module and a wearable article as claimed in claim 1.

20. The wearable article as claimed in claim 1, wherein the shape of the pocket space has four sides in which the fixed portion forms three sides.

* * * * *